US00PP08580P

United States Patent [19]

Kordes

[11] Patent Number: Plant 8,580

[45] Date of Patent: Feb. 8, 1994

[54] ROSE PLANT KORCILMO

[75] Inventor: Wilhelm Kordes, Sparrieshoop, Fed. Rep. of Germany

[73] Assignee: Bear Creek Gardens, Inc., Medford, Oreg.

[21] Appl. No.: 964,522

[22] Filed: Oct. 19, 1992

[51] Int. Cl.[5] ..... A01H 5/00

[52] U.S. Cl. ..... Plt./23

[58] Field of Search ..... Plt. 24, 26, 14, 23

*Primary Examiner*—Howard J. Locker
*Assistant Examiner*—Erich E. Veitenheimer
*Attorney, Agent, or Firm*—Klarquist, Sparkman, Campbell, Leigh and Whinston

[57] ABSTRACT

Floribunda rose capable of very high production of white blooms in a greenhouse and which have a long vase life.

1 Drawing Sheet

The present invention relates to a new and distinct variety of rose plant of the Floribunda class which was originated by me by crossing the variety KORenlo, U.S. Plant Pat. No. 5,679, with the variety KORampa, U.S. Plant Pat. No. 5,411.

The primary objective of this breeding was to produce a new rose variety having high production and a good vase life. The objective was substantially achieved along with other desirable improvements as evidenced by the following unique combination of characteristics which are outstanding in the new variety and which distinguish it from its parents, as well as from all other varieties of which I am aware:

1. Very high production in greenhouse of flowers (300 stems per $m^2$)
2. Small thorns
3. Excellent vase life
4. High vigor and ease of production as a cut flower Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—KORenlo, U.S. Plant Pat. No. 5,679.

*Pollen parent.*—KORampa U.S. Plant Pat. No. 5,411.

Classification:

*Botanical.*—*Rosa hybrida.*

*Commercial.*—Floribunda.

FLOWER

Observations made from specimens grown in a greenhouse environment in Somis, Calif. from March–June of 1992.

Blooming Habit: Recurrent.

Bud:

*Size.*—1¼" long when the petals start to unfurl.

*Form.*—The bud form is: Long pointed ovoid.

*Color.*—When sepals first divide, bud color is Yellow White Group 158B. When half blown, the upper sides of the petals are Yellow White Group 158D; and the lower sides of the petals are Yellow White Group 158D.

*Sepals.*—Color: Green Group 138B. Surface texture: Covered with fine hairs. There are three normally appendaged sepals. There are two unappendaged sepals with hairy edges.

*Receptacle.*—Color: Green Group 137D. Shape: Funnel. Size: Long, ⅜" long×2/8" wide. Surface: Smooth.

*Peduncle.*—Length: Medium, 2½". Surface: Smooth. Color: Medium Green. Strength: Stiff, erect.

Bloom:

*Size.*—Medium. Average open size is 3" in width when the petals are fully expanded. The fully open flower has a depth of 1 inch.

*Borne.*—Singly or several together in clusters. If in clusters: Rounded, with from 2 to 4 blooms per cluster.

*Stems.*—Medium (16–20"), strong.

*Form.*—When first open: High centered. Permanence: Retains its form to the end, outer petals curl back in a quill fashion.

*Petalage.*—Number of petals under normal conditions: 30–35.

*Color.*—The upper side of the petals is Yellow White Group 158D. The reverse side of the petals is Yellow White Group 158D. The bases of the petals have a very small greenish white half moon (⅛"×⅛") at the point of attachment. The major color on the upper side is Yellow White Group 158D.

*Variegations.*—Occasional Green streak on two outside guard petals.

*Discoloration.*—The general tonality at the end of the first day: No change. At the end of the third day, Change in color from Yellow White 158B in the bud stage to Yellow White 158D in the open flower.

*Fragrance.*—Slight.

Petals:

*Texture.*—Thick, leathery.

*Shape.*—Deltoid.

*Form.*—Tips slightly recurved, moderately quilled.

*Arrangement.*—Imbricated, with a few petaloids in the center.

*Persistence.*—Drop off cleanly.

*Lastingness.*—On the plant: Very long, 7 days. As a cut flower: Very long, 10 days.

Reproductive parts:

*Anthers.*—Size: Medium. Quantity: Many. Color: Yellow. Arrangement: Regular around styles.

*Filaments.*—Color: White.

*Pollen.*—Color: Gold yellow.

*Styles.*—Color: Reddish.

*Stigmas.*—Color: Greenish white.

Form: Bush. This plant is intended as a greenhouse cut-rose variety. Plant height and spread will be controlled by a cut-flower grower. In such an environment, height can range from 3 feet to 6 feet, and the spread controlled to a width of between 3 feet and 4 feet.

Growth: Very vigorous, upright and branching.

Foliage: Number of leaflets on normal mid-stem leaves: 5 or 7.

*Size.*—Large, 6″×4½″.

*Quantity.*—Abundant.

*Color.*—New foliage: Reddish. Old foliage: Upper surface: Green Group 137A. Lower surface: Green Group 139C.

Leaflets:

*Shape.*—Pointed oval.

*Texture.*—Upper side: Smooth.

*Edge.*—Serrated.

*Serration.*—Single, small.

*Petiole rachis.*—Color: Green.

*Petiole underside.*—Smooth with occasional prickles.

*Stipules.*—Short, bearded.

*Disease resistance.*—Susceptible to mildew under normal growing conditions at a greenhouse in Somis, Calif.

Wood:

*New wood.*—Color: Light Green. Bark: Smooth.

*Old wood.*—Color: Green. Bark: Smooth.

Prickles:

*Quantity.*—On main canes from base: Few. On laterals from main canes: Few.

*Form.*—Medium, hooked slightly upward.

*Color when young.*—Red.

Small prickles:

*Quantity.*—On main stalks: None. On laterals: None.

I claim:

1. A new and distinct variety of rose plant of the floribunda class, substantially as herein shown and described, characterized particularly as to novelty by the unique combination of its very high production of stems per $m^2$ of greenhouse, its long vase life, its small thorns and its overall high vigor and ease of production as a cut flower.

* * * * *

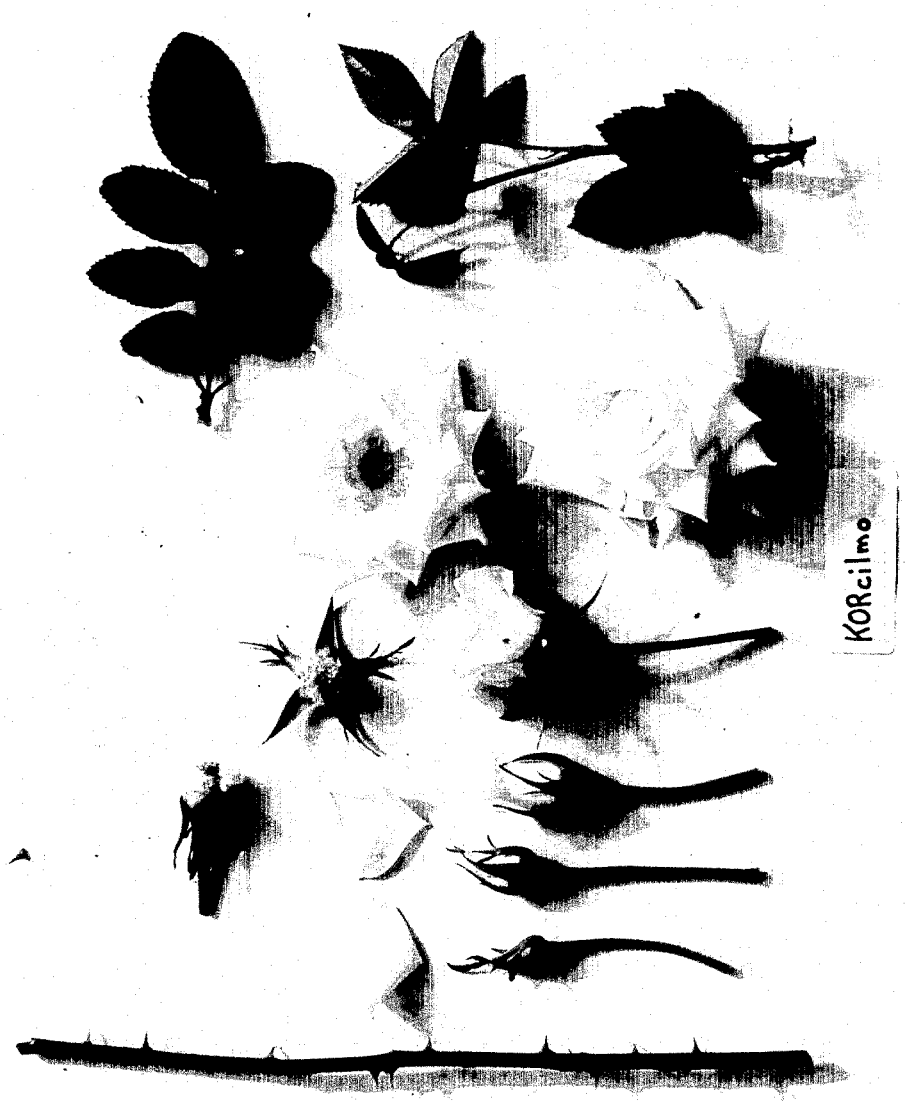
KORcilmo